(12) United States Patent
Duche

(10) Patent No.: US 7,691,114 B1
(45) Date of Patent: Apr. 6, 2010

(54) DEVICE FOR PROTECTING NERVES AFTER SURGICAL PROCEDURE

(75) Inventor: Renaud Duche, 7Bis, Chemin de la Musardiere, Villeneuve-les-Avignon (FR) F-30400

(73) Assignees: Renaud Duche, Villeneuve-les-Avignon (FR), part interest; Philippe Crepin, Saint-Dezery (FR), part interest ( * ) Notice: Subject to any disclaimer, the term of this patent is extended or adjusted under 35 U.S.C. 154(b) by 1462 days.

(21) Appl. No.: 10/129,816

(22) PCT Filed: Nov. 9, 2000

(86) PCT No.: PCT/FR00/03117

§ 371 (c)(1),
(2), (4) Date: Sep. 16, 2002

(87) PCT Pub. No.: WO01/35866

PCT Pub. Date: May 25, 2001

(30) Foreign Application Priority Data

Nov. 19, 1999 (FR) .................................... 99 14547

(51) Int. Cl.
*A61B 17/08* (2006.01)
(52) U.S. Cl. ..................................................... 606/152
(58) Field of Classification Search ......... 606/152–155, 606/69–71, 74, 76, 77, 213–215, 232, 151; 623/13.15, 13.16, 13.11, 13.14, 13.17, 13.18, 623/14.12, 17.19; 424/422–425
See application file for complete search history.

(56) References Cited

U.S. PATENT DOCUMENTS

| | | | | |
|---|---|---|---|---|
| 3,254,650 A | * | 6/1966 | Collito ........................ | 606/153 |
| 3,545,008 A | * | 12/1970 | Bader, Jr .................. | 623/13.15 |
| 4,329,743 A | * | 5/1982 | Alexander et al. ........ | 623/13.18 |
| 4,769,038 A | * | 9/1988 | Bendavid et al. .......... | 623/13.11 |
| 4,795,475 A | * | 1/1989 | Walker ......................... | 606/76 |
| 5,013,315 A | * | 5/1991 | Barrows ....................... | 606/71 |
| 5,084,051 A | * | 1/1992 | Tormala et al. ................ | 606/77 |
| 5,104,400 A | | 4/1992 | Berguer et al. | |
| 5,122,151 A | * | 6/1992 | de Medinaceli .............. | 606/152 |
| 5,413,577 A | * | 5/1995 | Pollock ........................ | 606/69 |
| 5,593,441 A | * | 1/1997 | Lichtenstein et al. ......... | 606/151 |
| 5,800,544 A | * | 9/1998 | Demopulos et al. ....... | 623/13.13 |
| 5,853,413 A | * | 12/1998 | Carter et al. ................... | 606/69 |
| 6,350,284 B1 | * | 2/2002 | Tormala et al. ........... | 623/17.19 |
| 6,743,243 B1 | * | 6/2004 | Roy et al. ..................... | 606/213 |

FOREIGN PATENT DOCUMENTS

GB        2 324 471        10/1998

* cited by examiner

*Primary Examiner*—Julian W Woo
(74) *Attorney, Agent, or Firm*—Young & Thompson

(57) ABSTRACT

The technical field of the invention is the manufacture of surgical equipment implantable in the human body. The invention concerns a device for protecting nerves (2) and/or tendons (3) located in a canal zone (13) of the human body, normally closed by a ligament (1) and which is opened during a surgical procedure. The invention is characterized in that the device includes at least a plate (10) whereof the dimensions enable its insertion between the edges of the ligament, and in particular whereof the length is compatible with the distance separating the edges (11) of the ligament (1) after the cut performed during the surgical procedure, and whereof one face (102) includes a sliding surface and the other face (101) a adhering surface, the plate (10) is preferably convex with two curvilinear sides parallel in the direction transverse to the sides corresponding to the cut edges (11) of the ligament (1).

4 Claims, 4 Drawing Sheets

DEVICE FOR PROTECTING NERVES AFTER SURGICAL PROCEDURE

This application is a 371 of PCT/FR00/03117, filed Nov. 9, 2000, which claims the benefit of French application no. 99/14547, filed Nov. 19, 1999.

BACKGROUND OF THE INVENTION

The subject of the present invention is a device for protecting nerves after a surgical procedure.

The technical field of the invention is the manufacture of surgical equipment implantable in the human body.

One of the main applications of the invention is the manufacture of a device for protecting the median nerve and the flexor tendons of the hand, in the area of the tunnel zone of the wrist which constitutes the carpal tunnel and which is delimited by the bones of said carpal tunnel (the carpal bones) and the corresponding anterior annular ligament.

Individuals who have to perform repetitive movements of the hand may develop inflammation of the synovial tissue which surrounds the tendons, with proliferation of fibrous synovitis. The tendons are then ensheathed and the internal volume of the tunnel increases, making the fingers insensitive after a certain period of time, as a result of compression of the median nerve, and making it impossible to carry out manual work thereafter. One of the surgical solutions employed at present, and the most effective for reducing this inflammation, is to treat the carpal tunnel syndrome by surgically opening said ligament to relieve the compression on the carpal tunnel and to remove the synovial fluid which has developed there: more than 60,000 operations of this type are performed each year in France, and for each person this means at least two months off work before being able to recover complete use of the hand.

However, on account of the opening of the transverse annular ligament, whose margins are thereby cut and are left floating, the flexor tendons of the fingers may leave the carpal tunnel and the median nerve is unprotected; the patient cannot therefore start using the hand again too soon, and, despite the precautions which are taken, a recurrence rate of 5% is observed.

To remedy this disadvantage, surgeons use different methods such as partial sectioning of one of the margins of the ligament in order to move it and connect it to the other margin, at the risk of tearing this ligament, which is in fact thereby weakened.

There is not in fact at present a satisfactory response to the postoperative problems created by opening the ligament, and this is the case regardless of the tunnel zone concerned, whether the wrist, which is the most common case, or the elbow or the ankle.

SUMMARY OF THE INVENTION

According to the present invention, a solution to the problems posed is a device for protecting nerves and/or tendons located in any tunnel zone of the human body which is normally closed by a ligament and has been opened during a surgical procedure. According to the invention, the device comprises at least one rigid or semirigid plate which is intended to be inserted between the cut edges of said ligament, after cutting during said surgical procedure, and of which one face comprises a sliding surface and the other face comprises an adhering surface.

The expression "semirigid plate" is to be understood as meaning that this plate is capable of maintaining a tile shape in particular, when it has been produced in particular by molding in the case where the plate is made of synthetic material. However, it must be understood that the plate can have a certain elasticity, that is to say it can undergo deformation, particularly at the time of its implantation, and then return to its initial shape.

The expression "sliding surface" is to be understood as meaning a smooth surface, in particular without any roughening or bumps, and with a low coefficient of friction, so as not to prevent the movement of the nerve and tendons relative to said plate.

The expression "adhering surface" is to be understood as meaning a surface which has a texture and/or a roughness, in particular a porosity, such as to promote the regrowth of biological tissues, in particular of the sectioned ligaments, by attachment of fibroblasts which are able to recolonize said surface.

To permit insertion of the plate between the cut edges of said ligament after cutting, the plate must advantageously have a shape and dimensions adapted respectively to the site of implantation, that is to say to the shape of the tunnel zone, and to the cut which is made.

In particular, the dimensions of the plate must permit its insertion between the cut edges of the ligament. The length and the width preferably correspond to the opening in the ligament and in particular to the distance separating said edges after cutting, the length of the plate therefore being at most equal to that of the opening.

The shape of said plate preferably corresponds to the anatomical shape of the tunnel zone at the site of insertion. In particular, it can have a flat shape or a bulged shape.

When said plate has a bulged shape, said sliding surface is located on its concave face, and said adhering surface is located on its convex face.

In one embodiment, said plate has a bulged shape with at least two parallel curvilinear sides in the direction transverse to the sides corresponding to the cut edges or margins of the ligament.

For a protection which is more particularly adapted to the tunnel zone of the wrist, said plate has a tile shape, that is to say in the shape of a cylindrical cap with two parallel rectilinear sides in the longitudinal direction corresponding to the cut edges of said ligament, and two parallel curvilinear sides in the transverse direction.

Said plate can also be a tile of frustoconical shape with only the two curvilinear sides parallel.

For adaptation to other tunnel zones, for example to the elbow, said bulged plate must not have a cylindrical cap shape but a surface of revolution with double curves, that is to say with 4 parallel curvilinear sides arranged in pairs, in order to follow the profile of the tunnel.

In a particular embodiment, the four corners of said plate define a rectangle of which the length is less than the size of the cut and of which the width/length ratio is from ¼ to ¾, preferably ⅓ to ⅔.

More particularly, said plate has a length of 10 to 25 mm and a width of 3 to 15 mm.

Likewise, said plate preferably has a thickness almost equal to that of said cut ligament.

Said plate according to the invention is made of biomaterials, that is to say materials which can be implanted in the human body without risk of rejection. Biomaterials are well known to the person skilled in the field of surgery.

To be able to maintain this continuity after it has been put into place, said plate 10 is of sufficient rigidity to retain its shape, in particular its bulged shape, by itself. This rigidity can be obtained using a material such as metal, which can be used for part of said plate, in particular its sliding surface, or using a synthetic elastomer such as silicone or polyurethane, its thickness then having to be preferably of the order of 1 to 3 mm in order to give sufficient rigidity to said plate.

Preferably, in order to achieve the desired results, said plate is produced using two layers of biomaterials with different sliding and adhering properties, which are joined to each other and which each respectively constitute the sliding surface and the adhering surface.

The biomaterials used can be absorbable, such as polylactic and polyglycolic polymers and copolymers, and in particular the biomaterial corresponding to the adhering surface 101 involved in reformation of the tissues, which will ensure closure of the carpal tunnel after regrowth, is advantageously an absorbable material.

The roughness Ra of the sliding surface is preferably less than 4 microns, in particular from 0.5 to 4 microns, preferably less than 3.2 microns, still more preferably less than 0.8 micron. The roughness Ra is known to the person skilled in the art: it corresponds to an arithmetic mean deviation of the peaks and valleys of the surface in relation to a mean line.

The roughness of the adhering surface is preferably defined by a roughness Rt of at least 50 microns, preferably at least 100 microns. The roughness Rt corresponds to the maximum total deviation between the summit of the peaks and the bottom of the valleys of the surface texture.

In an advantageous embodiment, the sliding surface is made of a biocompatible elastomer, in particular polyurethane or silicone.

Likewise, the adhering surface is advantageously made of a biocompatible polymer with a microporous structure, in particular a fibrillar structure, such as a material made up of polyester fibers. Said microporous structure has pores with an average size of preferably from 50 to 600 microns.

Said plate is advantageously made of elastomer, in particular silicone or polyurethane covered on one face with a lattice of fiber filaments of a biocompatible polymer, in particular polyester, anchored on said face. Lattice is here understood as a fabric of multifilaments of synthetic fibers with openworked meshes.

In one embodiment, the plate comprises 5 to 40% by weight of microporous material, in particular polyester in a lattice shape, and 60 to 95% by weight of biocompatible elastomer, in particular silicone, the total amounting to 100%.

The plate is preferably made of absorbable material(s).

To ensure that said plate is held in the opening in the ligament, it can comprise at least four holes to ensure suturing thereof to the edges of the ligament, or at least four hooks which can be anchored in the edges of the ligament.

In an advantageous embodiment allowing the plate to be laced, the plate comprises oblique holes, that is to say holes whose axis is inclined.

The plate can also be secured to the edges of the ligament by a means such as staples.

The result is a novel device for protecting nerves and/or tendons located in any tunnel zone of the human body, such as that of the wrist, but which can be applied in any other tunnel zone. This device satisfies the problems posed since, on the one hand, it maintains the continuity of the annular ligament, which can thus heal all the more quickly, and, on the other hand, during this healing, it ensures that the nerves and tendons located in the tunnel zone cannot escape from the latter. Moreover, the face having the sliding surface and arranged toward the tunnel zone permits a freedom of movement of the tendons located there, while the opposite face corresponding to the adhering surface and arranged on the top, i.e. toward the skin, thus permits more rapid regrowth of the tissues and thus the healing.

Thus, the device of the invention at the same time permits closure of the tunnel zone, protection of the nerves and tendons, stabilization of the margins of the ligament, and preservation of the volume of the tunnel zone. There is therefore a noticeable reduction in the recovery time, much less than the two months required at present, with a reduction in the rate of recurrences and in the pain suffered by the patients.

Other characteristics and advantages of the present invention will become evident on reading the following detailed description.

BRIEF DESCRIPTION OF THE DRAWINGS

The description and the attached figures represent an illustrative embodiment of the invention but are not limiting in nature. Other embodiments are possible within the scope and range of the present invention, in particular for applications in other tunnel zones of the human body, although the example described in FIG. 1, and which is the main application of the present invention, concerns surgery of the hand.

DETAILED DESCRIPTION OF THE PREFERRED EMBODIMENTS

Figure 1:
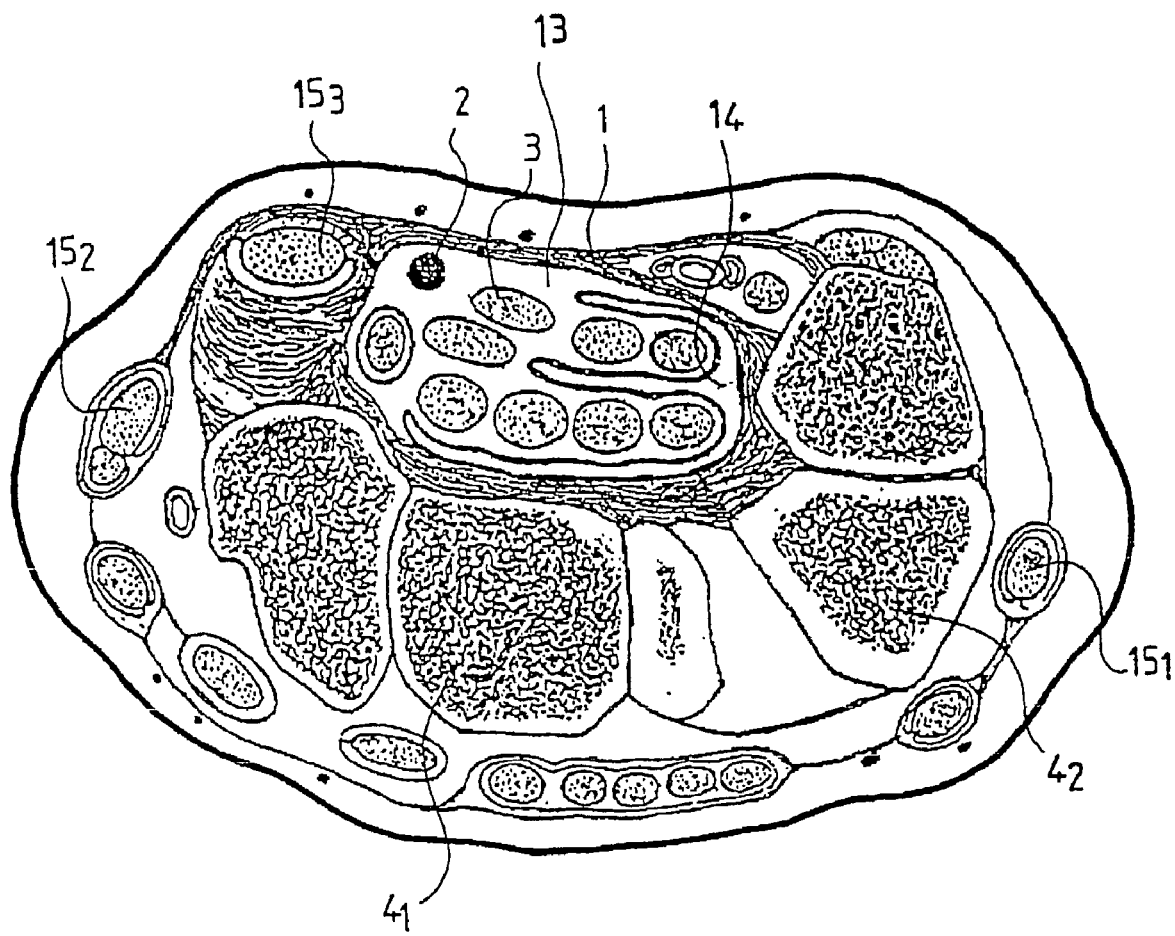
FIG. 1 is a cross-sectional view of the region of the wrist.
Figure 2:
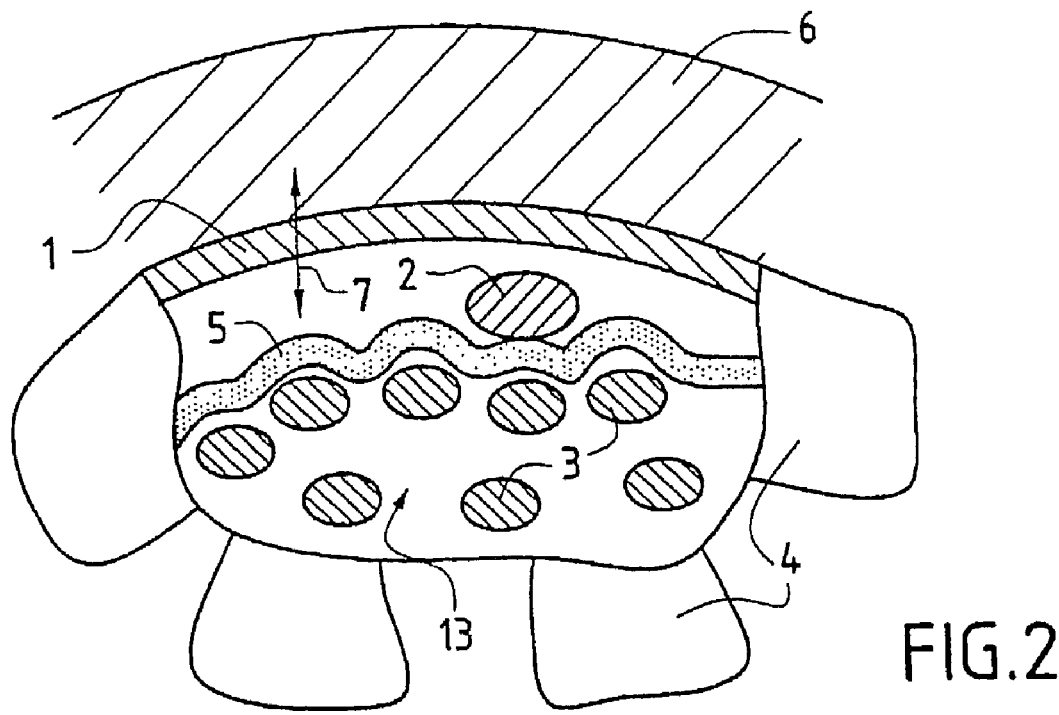
FIG. 2 is a simplified cross-sectional view of a wrist before a surgical procedure in which the device for protecting nerves according to the invention can be used.

According to FIGS. 1 and 2, the bones of the wrist or carpus 4 define, with the anterior annular ligament 1 of the carpus, a tunnel zone 13 through which the median nerve 2 and the flexor tendons 3 run.

The flexor tendons 3 are protected by an internal digitocarpal sheath 14. The tunnel zone 13 is surrounded by the various bones of the wrist 4, which themselves are surrounded by the extensor tendons 15 of the wrist.

An inflammation of the synovial tissue which surrounds the tendons 3 can cause synovitis 5 (of the flexors) which, as it develops, blocks said tendons 3 and compresses the median nerve 2. To relieve the compression on this zone, it is possible to cut 7 said ligament 1 via an opening made in the overlying skin 6 in order, on the one hand, to increase the volume of the tunnel zone 13 and, on the other hand, to remove the synovial substance 5 by this direct procedure.

Figure 3:
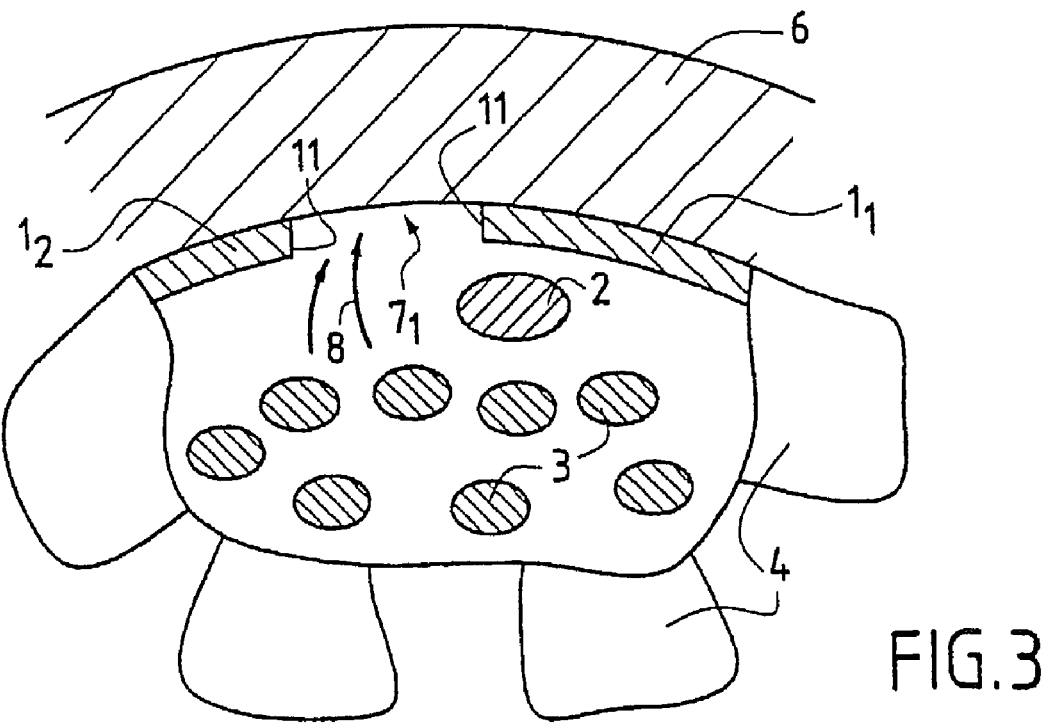
FIG. 3 is a partial cross-sectional view of the wrist in FIG. 1, after a surgical procedure, but without the device according to the invention.

After said procedure, the margins $1_1$ and $1_2$ of the ligament, which remain open and floating, may allow escape 8 of the tendons 3 and possibly also of the nerve 2 through the opening $7_1$ which has thus been left wide open, as is shown in FIG. 3.

To overcome this problem and also those mentioned above, the device for protecting nerves 2 and/or tendons 3 according to the invention comprises at least one plate 10 whose shape and dimensions, in particular the width, are compatible with the distance separating the edges 11 of the margins $1_1$ and $1_2$ of said ligament 1 after cutting 7, and of which one face $10_2$ has a sliding surface and the other face $10_1$ has an adhering surface.

To permit its insertion between the two margins $1_1$ and $1_2$ of the ligament and to restore the continuity of the ligament 1, the dimensions of said plate 10 preferably correspond as exactly as possible to those of the opening $7_1$ in the ligament 1, and its thickness is almost equal to that of this ligament 1.

Given that the opening is made a priori in a straight line, said plate 10 is thus of rectangular shape and, in order to ensure better continuity with the shape of the ligament and to restore the volume of the carpal tunnel 13, said plate 10 has a bulged shape with two parallel curvilinear sides in the direction transverse to the sides corresponding to the cut edges 11 of the ligament 1, thereby giving it a "tile" shape.

In a suitable manner, said plate has a tile shape of the cylindrical cap type with a length of the two parallel rectilinear sides of 10 to 25 mm, and a curvature of the two parallel curvilinear transverse sides, in an arc of a circle or ovoid shape, having a radius of curvature of 5 to 10 mm, in particular 7 mm, and chord lengths corresponding to said curvatures of 5 to 15 mm. More particularly, plates are made with a length of 12 and 15 mm and a width of 5, 6, 7 and 8 mm.

Plates with these dimensions (cylindrical caps) can be adapted to all types of patients and to all types of incision, it being understood that, even for larger incisions, a plate which is smaller than the incision nevertheless fulfills the function of protection which is sought.

Figure 6A:
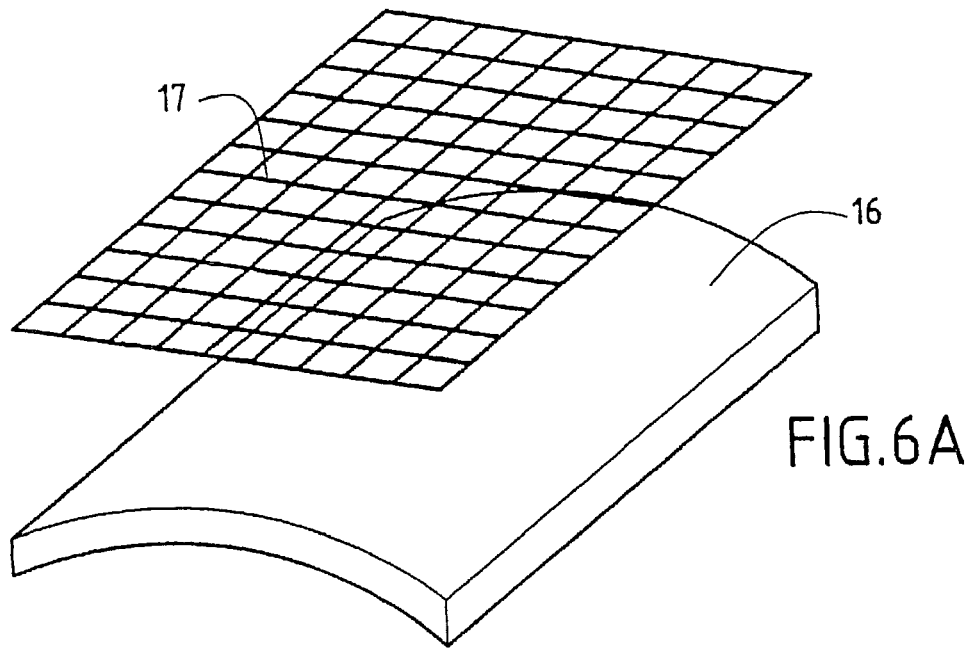
FIGS. 6a and 6b show a device made from a lattice of fibrillar structure anchored to the surface of an elastomer.
Figure 6B:
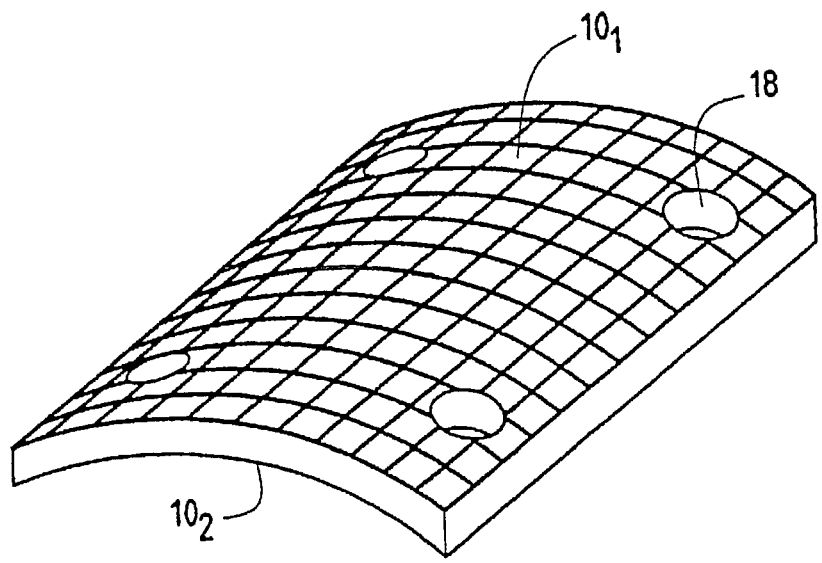

To form said sliding and adhering surfaces shown in FIGS. 6a and 6b, nonabsorbable materials have been used, such as silicone for the sliding surface, and biocompatible polymers in the form of a fibrillar structure, such as polyester terephthalate fibers, for the adhering surface.

In this embodiment in FIGS. 6a and 6b, said plate is made up of a layer of silicone 16 which has, anchored on its surface, on a face which will thus constitute the adhering surface, a lattice 17 of polyester fibers, particularly of PET, the fibrillar structure of which has a porosity characterized by a mean size of the pores of between 50 and 600 microns. The lattice of polyester polymer fibers is applied to the surface of the plate of silicone during formation and is anchored to its surface after complete polymerization of the silicone.

It is not the macro-texture thereby created on the surface of the silicone on one of the faces which confers adhering properties to said face, but instead the roughness or micro-porosity of the material of fibrillar structure constituting said lattice.

In this embodiment in FIGS. 6a and 6b, a plate has been produced with a silicone thickness of 1.5 mm covered by a polyester fiber lattice of 0.5 mm thickness, said plate being 6% polyester and 94% silicone.

The plate in FIGS. 6a and 6b is made from a lattice of PET. Multifilament tissues of polyester fibers with openworked meshes, such as a knit 16, are known to the person skilled in the art. They are used in surgery in the form of a knit with openworked meshes made of polyethylene terephthalate (PET). These mesh knits are flexible and are used as such as flexible implants for the restoration of walls. In some cases, the polyester filaments are impregnated with silicone, but the openworked knit structure is retained. However, the surface roughness associated with the microporosity of the fibrillar structure is not retained.

In the embodiment according to the invention, the polyester filaments are not totally impregnated with silicone and they retain a microporosity on one of their faces not covered by silicone.

A plate according to FIGS. 6a and 6b can therefore be obtained in the following way: the lattice of PET fibers is placed in the bottom of a mold of bulged shape corresponding to the shape desired for said plate. The elastomer compound, in particular silicone, is injected at low pressure in such a way as to fill the mold without completely covering the PET lattice. Partial coating of the lattice means that the face opposite the mold can be left uncovered by silicone, while at the same time anchoring said lattice to the silicone surface, after polymerization of the latter.

Said plate 10 can also be made of a single material, and the two faces, namely the upper face oriented toward the skin 6 and the lower face oriented toward the tunnel zone 13, will be treated in order to obtain the desired adhering surface and sliding surface, respectively.

If a plate made of metal is used, as was mentioned previously, the adhering surface can be obtained by treating the metal surface in such a way as to give it a micro-texture or roughness, in particular with a value of Rt of at least 50 microns, preferably at least 100 microns.

Figure 4A:
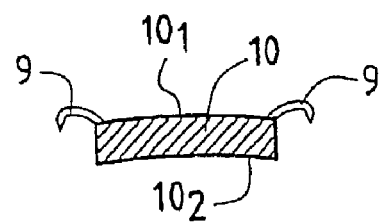
FIGS. 4A and 4B show a cross-sectional view and a plan view, respectively, of a device according to the invention.
Figure 4B:
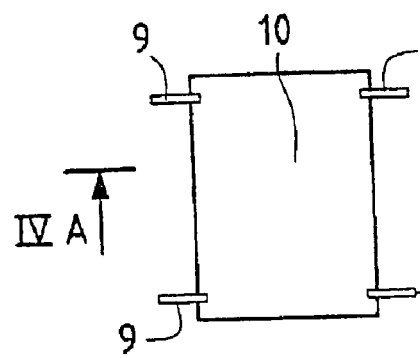
Figure 5:
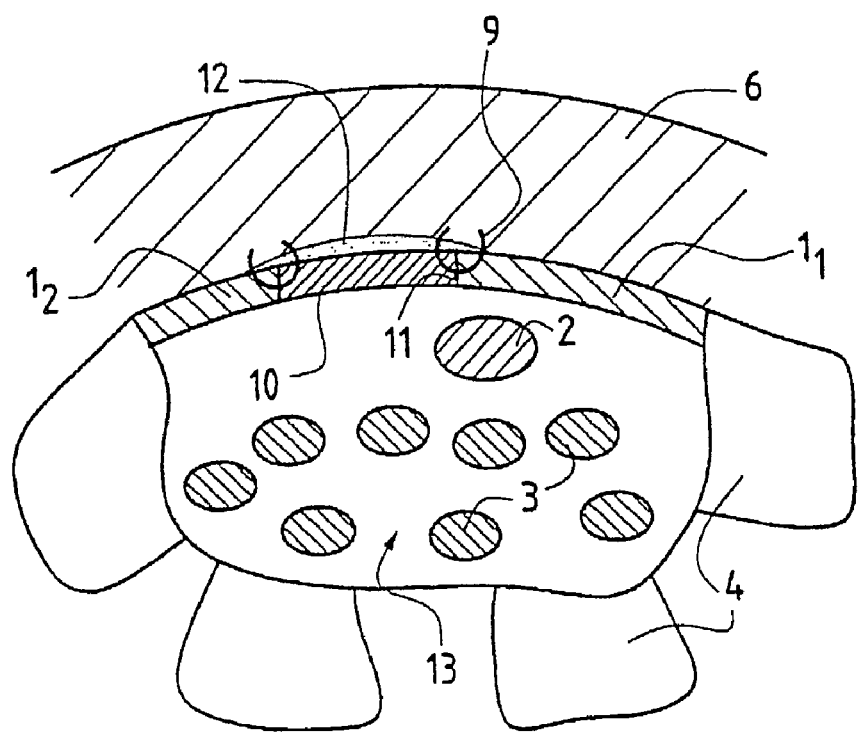
FIG. 5 is a partial cross-sectional view corresponding to that in FIG. 2, but after a device according to the invention has been fitted.
Figure 7:
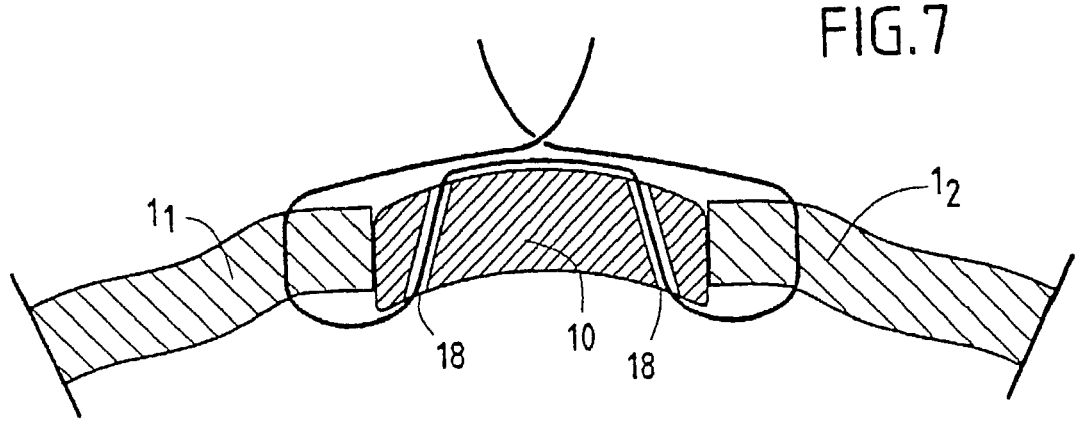
FIG. 7 shows a device comprising inclined holes allowing it to be laced with suture elements.

To ensure fixation of the plate 10 between the margins $1_1$ of the cut ligament, this plate can comprise either at least four holes 18 which are perpendicular to the sliding surface and adhering surface and ensure suturing 12 thereof to the edges 11 of the ligament 1, as is shown in FIG. 6b, or at least four hooks 9 which can be anchored directly in the edges 11 of the ligament 1, as is shown in FIGS. 4a, 4b and 5. This plate can also comprise at least four holes 18 which are inclined (not perpendicular) with respect to the sliding surface and adhering surface. The inclination makes it possible to recede the stresses transmitted by the suturing elements, which can thus be laced as shown in FIG. 7.

The inclination can vary depending on the thickness and the width of the plate. The angle of the inclination is such that the lower end of the holes is nearer to the adjacent lateral edge of the plate than is the upper end.

The invention claimed is:

1. A device for protecting nerves and/or tendons located in a tunnel zone of the human body which is normally closed by a ligament and has been opened during a surgical procedure, said device comprises means for permitting freedom of movement of nerves and/or tendons while protecting nerves and/or tendons, which is intended to be inserted between edges of a ligament after cutting; and means for anchoring said means for permitting freedom of movement while protecting.

2. The device for protection as claimed in claim 1, wherein said means for permitting freedom of movement while protecting has a thickness almost equal to that of a ligament at the site of said procedure.

3. The device for protection as claimed in claim 1, wherein dimensions of said means for permitting freedom of movement while protecting correspond to those of an opening in a ligament, a length of the means for permitting freedom of movement while protecting being at most equal to that of a cut in a ligament.

4. A device for protecting nerves and/or tendons located in a tunnel zone of the human body which is normally closed by a ligament and has been opened during a surgical procedure, said device comprises:

at least one rigid or semi-rigid continuous plate which is intended to be inserted between edges of a ligament after cutting and, one external face of said plate comprises a sliding surface and another external face of said plate comprises an adhering surface, wherein said sliding surface comprises a biocompatible material, wherein said adhering surface comprises a biocompatible material in the form of a fibular lattice, and wherein said plate has a bulged shape with said sliding surface on a concave face of said plate and said adhering surface on a convex face of said plate.

* * * * *